(12) United States Patent
Chandler

(10) Patent No.: US 6,905,766 B2
(45) Date of Patent: Jun. 14, 2005

(54) ENCAPSULATION OF DISCRETE QUANTA OF FLUORESCENT PARTICLES

(75) Inventor: Don J. Chandler, Austin, TX (US)

(73) Assignee: Luminex Corporation, Austin, TX (US)

(*) Notice: Subject to any disclaimer, the term of this patent is extended or adjusted under 35 U.S.C. 154(b) by 54 days.

(21) Appl. No.: 10/355,073

(22) Filed: Jan. 31, 2003

(65) Prior Publication Data

US 2003/0132538 A1 Jul. 17, 2003

Related U.S. Application Data

(63) Continuation of application No. 10/103,807, filed on Mar. 25, 2002, now Pat. No. 6,528,165, which is a continuation of application No. 09/639,819, filed on Aug. 17, 2000, now abandoned.
(60) Provisional application No. 60/149,227, filed on Aug. 17, 1999.

(51) Int. Cl.[7] ............................. B32B 15/02; B01J 13/02
(52) U.S. Cl. ................... 428/402.2; 264/4.1; 264/4.3; 264/4.33; 264/4.4; 264/4.7; 428/402.21; 428/403; 428/690
(58) Field of Search .................. 264/4.1, 4.3, 4.33, 264/4.4, 4.7; 428/402.2, 402.21, 403, 690

(56) References Cited

U.S. PATENT DOCUMENTS

| | | |
|---|---|---|
| 3,404,093 A | 10/1968 | Borrows |
| 3,485,758 A | 12/1969 | Borucki et al. |
| 3,998,526 A | 12/1976 | Katz |
| 4,164,559 A | 8/1979 | Miyata et al. |
| 4,236,071 A | 11/1980 | Chimenti |
| 4,298,002 A | 11/1981 | Ronel et al. |
| 4,336,459 A | 6/1982 | Fay |
| 4,337,999 A | 7/1982 | Funada et al. |
| 4,341,997 A | 7/1982 | Borrows |
| 4,352,883 A | 10/1982 | Lim |
| 4,353,888 A | 10/1982 | Sefton |
| 4,365,153 A | 12/1982 | Seigel et al. |
| 4,374,120 A | 2/1983 | Soini et al. |
| 4,391,909 A | 7/1983 | Lim |
| 4,425,029 A | 1/1984 | Funada et al. |
| 4,454,106 A | 6/1984 | Gansow et al. |
| 4,534,317 A | 8/1985 | Walsh |
| 4,668,049 A | 5/1987 | Canter et al. |
| 4,673,566 A | 6/1987 | Goosen et al. |
| 4,677,045 A | 6/1987 | Champ et al. |
| 4,689,293 A | 8/1987 | Goosen et al. |
| 4,724,094 A | 2/1988 | Song |
| 4,803,168 A | 2/1989 | Jarvis, Jr. |
| 4,806,355 A | 2/1989 | Goosen et al. |
| 4,921,280 A | 5/1990 | Jalon |
| 5,017,501 A | 5/1991 | Wong |
| 5,039,206 A | 8/1991 | Wiltshire |
| 5,052,784 A | 10/1991 | Fergason |
| 5,182,111 A | 1/1993 | Aebischer et al. |
| 5,229,320 A | 7/1993 | Ugajin |
| 5,237,498 A | 8/1993 | Tenma et al. |
| 5,354,873 A | 10/1994 | Allen et al. |
| 5,482,890 A | 1/1996 | Liu et al. |
| 5,492,795 A | 2/1996 | Allen et al. |
| 5,525,516 A | 6/1996 | Krutak et al. |
| 5,573,909 A | 11/1996 | Singer et al. |
| 5,656,750 A | 8/1997 | Allen et al. |
| 5,760,201 A | 6/1998 | Glazer et al. |
| 5,795,981 A | 8/1998 | Lee et al. |
| 5,879,920 A | 3/1999 | Dale et al. |
| 5,888,885 A | 3/1999 | Xie |
| 5,895,795 A | 4/1999 | Hashemzadeh |
| 5,906,670 A | 5/1999 | Dobson et al. |

FOREIGN PATENT DOCUMENTS

| | | |
|---|---|---|
| WO | WO91/12530 A | 8/1991 |
| WO | WO99/19515 A | 4/1999 |
| WO | WO99/37814 A | 7/1999 |

OTHER PUBLICATIONS

US 4,487,758, 12/1984, Goosen et al. (withdrawn)
Sprenger et al., Agnew. Chem., vol. 79, pp. 581–582, 1967.
Sprenger et al., Agnew. Chem., vol. 80, pp. 541–546, 1968.
Maahs et al., Agnew. Chem. Internat. Edit., vol. 5, pp. 888–893, 1966.
Law et al., J. Org. Chem., vol. 57, pp. 3278–3286, 1992.
International Search Report PCT/US00/22537.
XP–002157474—Database WPI, Derwent Publications Ltd., London, GB.

Primary Examiner—Samuel A. Acquah
(74) Attorney, Agent, or Firm—Charles D. Hustop; Ann Marie Mewherter; Daffer McDaniel, LLP

(57) ABSTRACT

The present invention provides novel encapsulation compositions and methods. In particular, the invention relates to fluorescent capsule compositions, which consists of a layer of a polymer shell enclosing one or more fluorescent materials such as fluorescent microspheres and which are capable of emitting at least two distinct fluorescent signals. Also provided are methods for their preparation. The compositions and methods of this invention are useful in a variety of applications, including preparation of multiplexed arrays for industrial, chemical, immunological, and genetic manipulation and analysis especially as related but not limited to flow cytometry.

29 Claims, No Drawings

ENCAPSULATION OF DISCRETE QUANTA OF FLUORESCENT PARTICLES

1. RELATED APPLICATIONS

This application is a Continuation of 10/103,807, filed Mar. 25, 2002, now U.S. Pat. No. 6,528,165, which is a Continuation of 09/639,819, filed Aug. 17, 2000, now abandoned, which claims the benefit of 60/149,227, filed Aug. 17, 1999.

2. FIELD OF THE INVENTION

The present invention generally relates to novel encapsulation compositions and methods. In particular, the invention relates to fluorescent microcapsule compositions which comprise a layer of a polymer shell enclosing one or more particles capable of emitting at least two distinct fluorescent signals, and methods for their preparation. The compositions and methods of the invention are useful in a variety of applications, including preparation of arrays for industrial, chemical, immunological, and genetic manipulation and analysis.

3. BACKGROUND OF THE INVENTION

Fluorescently labeled particles are being used extensively in a wide range of applications. By combining two or more dyes and by varying each of fluorescent dyes' concentration and/or the emission wavelengths of the dyes, it is possible to create an almost infinite number of fluorescently distinguishable particles. These particles can subsequently be used as markers in such diverse applications as combinatorial chemistry, diagnostics, e.g., DNA analysis, and industry uses, e.g., liquid labeling of fluids.

One such technology, which is currently available, uses polystyrene microspheres into which are absorbed precisely controlled quantities of two or more fluorescent dyes. This requires dissolution of the dye in an organic solvent, which can then be added to the microspheres, thus inducing swelling of the particle and absorption of the dye. The microspheres are then isolated from the dye solution and excess dye removed by a wash step. However, there are several drawbacks to this system. The first is that the wash step usually removes some of the dye from the beads, which makes it difficult to predict the exact amount of dye to be absorbed. Another problem is that placing these dyed microspheres in organic solvents results in leaching of the dye into the surrounding environment. Additionally, this technique requires that the dye be soluble in an organic solvent, which precludes the use of water-soluble particulate fluorescent materials. It would therefore be a significant improvement if methods were devised to encapsulate a precisely controlled number of soluble or insoluble fluorescent particles or substances within a stable shell material encapsulating them.

Encapsulation is a well-known technique in the art for protecting components that are sensitive to the elements, for providing controlled release of capsule ingredients, and/or to prevent dust formation by non-encapsulated particles among many other applications.

U.S. Pat. No. 5,879,920 issued to Dale et al., discloses multi-layered enzyme-containing composition, which is coated with a vinyl polymer. This composition, which is intended to be used as a laundry detergent, is useful for preventing enzyme-containing dust formation that may be allergenic to those who handle it. Among many other substances, fluorescent dyes are described as adjunct ingredients that may be added to the enzyme powder. However, no combination of fluorescent dyes is described or suggested. The only reason for using fluorescent dyes in detergents is to make laundered fabrics look brighter. Finally, the polymer shell of the enzyme granule must be readily soluble in an aqueous solution to release the enzyme and additive such as a fluorescent dye.

U.S. Pat. Nos. 4,724,094 and 4,341,997 issued to Song and Borrows respectively, disclose methods of preparing a fluorescent magnetic composition useful for inspecting and detecting cracks and various small defects in metal work pieces. The preparation of such fluorescent/magnetic particles is spread on the surface of a metal piece and defects are identified under ultra-violet light or "black" light. The manufacturing of these particles involves a plasticizer in order to effect a more complete encapsulation of fluorescent pigment and magnetic particle powder by film-forming resin. Composition made by the inventive method are described, as well as methods of using the composition in non-destructive testing of magnetizable work pieces. This invention is not functional without magnetic particles and it does not require more than one fluorescent dye.

U.S. Pat. No. 4,534,317 issued to Walsh discloses two types of encapsulated food pellets containing fluorescent dyes. The first type, which when eaten by fish, causes the water to fluoresce, the second type disintegrates spontaneously causing the water to fluoresce when not eaten by fish. By administering food containing both types of fluorescent dyes simultaneously, and measuring the ratio of their respective fluorescence intensities, a sensitive measure of feeding activity is achieved. While two fluorescent dyes are used in this invention they are not present in the same capsule and ultimately these dyes are meant to be released in the aqueous environment.

The encapsulation techniques are also used in an unrelated field of entrapping of living cells in tiny microcapsules, which are then introduced into a host organism as a means of delivery of biologically important factors produced by such cells. Examples of microencapsulation devices can be found in U.S. Pat. No. 5,182,111, issued to Aebischer et al.; U.S. Pat. Nos. 4,487,758, 4,673,566, 4,689,293, and 4,806,355, each issued to Goosen et al.; U.S. Pat. No. 4,803,168, issued to Jarvis, Jr.; U.S. Pat. Nos. 4,352,883 and 4,391,909, both issued to Lim; U.S. Pat. No. 4,298,002, issued to Ronel et al.; and U.S. Pat. No. 4,353,888, issued to Sefton. However, the purpose and scope of these devices are not related to the instant technical field and thus the interior of these microcapsules does not contain fluorescent dyes.

The present inventor has provided a novel principle of encapsulating fluorescent materials in light-permeable, environment-stable capsules capable of emitting at least two distinct fluorescent signals.

4. SUMMARY OF THE INVENTION

This invention relates to the field of encapsulation whereby particles enclosed in a shell barrier are produced and said particles are capable of emitting two or more fluorescent signals. The invention relates to composition and methods of manufacturing particle-enclosing capsules. The particles themselves as a composition of matter comprises a precise mixture of a number of fluorescent materials, e.g., fluorescently distinct microspheres, crystals, nanocrystals, powders, liquid crystals, and the like, which are then encapsulated within a barrier or shell material.

The preferred composition of the invention comprises two or more substances, each substance capable of emitting a distinctive fluorescent signal and a shell barrier encapsulating these substances. It is preferable that fluorescent signals are distinctive by way of its wavelength, intensity, or both.

It is an object of this invention to provide a composition and methods of making such a composition available, whereby the composition contains fine fluorescent particles which are stable and capable of emitting discrete fluorescent signals during further processing of the composition, e.g., during flow cytometry analysis when exposed to a fluorescence excitation light. The invention relates to a composition containing fine fluorescent particles such as inorganic and organic spheres stained with discrete fluorescent dyes. These particles, besides being presented as spheres, may also presented in form of powders, crystals, rods, fibers, liquids, and the like, each encapsulated by a barrier to form a light-permeable capsule or dispersed in a matrix whereby the barrier and/or the matrix consists of a polymerizable material and, if necessary, of other additional components that will deter the leakage of the fluorescent dyes or fluorescent constituents from the capsule or matrix.

The present invention also provides methods for producing capsules or matrices that preferably emit two or more signals of precisely controlled intensities. This is accomplished by encapsulating soluble or insoluble fluorescent materials within a barrier material or by dispersing within a non-leakable matrix, the outer surface of which constitutes the barrier per se. Fluorescent materials may be in a number of forms, including dye absorbed in small polymeric spheres, granules, fibers, dye dissolved in a solvent, amorphous powders, or crystals, such as CdS.

It is preferable that encapsulation material chosen for application are compatible with the application; that is, if the particles are to be used in a particular solvent, the shell material must be stable in that solvent. The outer coating layer (shell) of the present invention preferably comprises between about 1–20% by weight of the interior matrix.

Examples of potentially useful and preferable shell materials are: gelatin, gum arabic, collagen, casein, polystyrene, and other art-known polymeric materials that will serve to deter migration of the fluorescent materials from the capsule. Such materials are well known in the art, including but not limited to: chitosan, polycarboxylated polymer, hydrophilic gums and hydrophilic mucilloids such as agar, alginic acid, calcium polycarbophil, cellulose, carboxymethylcellulose sodium, carrageenan, chondrus, glucomannan, polymannose acetate, guar gum, karaya gum, kelp, methylcellulose, plantago seed (psyllium), polycarbophil tragacanth, pectin, starch, tragacanth gum, xanthan gum or acidic fractions thereof, monoalkylene glycol monoester of methacrylic acid, polyalkylene glycol monoester of methacrylic acid, monoalkylene glycol monoester of a crylic acid, polyalkylene glycol monoester, N-alkyl substituted acrylamide, N,N-dialkyl substituted acrylamide, N-alkyl substituted methacrylamide, N,N-dialkyl substituted methacrylamide, N-vinylpyrrolidone, alkyl substituted N-vinylpyrrolidone, vicinal epoxy alkyl 2-alkenoate, and combination thereof among them or with many other materials. For example, in addition to polystyrene, polymeric materials will include but are not limited to brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polysulfone, or combinations thereof are acceptable as well. Other materials such as carbohydrate, e.g., hydroxyethyl cellulose, proteinaceous polymers, polypeptides, lipids (liposomes), metal, resin, latex, rubber, silicone, e.g., polydimethyldiphenyl siloxane, glass, ceramic and the like are equally suitable. The various encapsulation techniques using these materials are well documented in encapsulation art and are familiar to those skilled in the art.

The fluorescent emission profile can be specified by two methods, each of which accomplishes this by manipulating the amount of fluorescent material in the capsule. One technique uses capsule size to dictate the fluorescent emission. A mixture of soluble and/or insoluble fluorescent particles at specific concentrations is prepared, then agitation is applied during the encapsulation process. Thus, in a preferred particle making method, numerous sets of differently sized microcapsules containing the fluorescent substances are made by varying the agitation rate. In this manner, for a given starting concentration of fluorescent substances, the larger capsules would have more intense fluorescent emissions than smaller capsules. Another advantage is that particle size serves as an additional parameter with which various capsule populations are differentiated. The preferred size range of capsules is anywhere from about 1 nanometer (nm) to about 10 millimeters (mm). A more preferred size range is from about 1 micrometer (micron) to about millimeter (mm) or 1,000 microns.

Another preferred technique to create multiple, distinguishable populations of fluorescent particles is to simply vary the concentration of fluorescent emitters in uniformly sized capsules. This is accomplished by diluting the fluorescent phase with non-fluorescent material. By varying the degree of dilution of a given fluorescent mixture, as well as varying the concentrations of fluorescent materials relative to each other, a large population of distinguishable particles is manufactured.

5. DETAILED DESCRIPTION OF SPECIFIC EMBODIMENTS

A large number of materials and techniques can be used to form the microcapsules, which are familiar to those skilled in the art. A variety of microencapsulation methods and compositions are known in the art. These compositions are primarily used in pharmaceutical formulations, for example, to mask the taste of bitter drugs, formulate prolonged dosage forms, separate incompatible materials, protect chemicals from moisture or oxidation, or modify the physical characteristics of the material for ease of handling and/or processing. Typical pharmaceutical encapsulation compositions include, e.g., gelatin, polyvinyl alcohol, ethylcellulose, cellulose acetatephthalate and styrene maleic anhydride. See Remington's Pharmaceutical Sciences, Mack Publishing Co., Easton Pa. (1990). Microencapsulation has also been applied in the treatment of diseases by transplant therapy. Exemplary methods and materials are described hereinafter.

The encapsulation materials chosen for application must be compatible with the application, that is, if the particles are to be used in a particular solvent, the shell material must be stable in that solvent. The outer coating layer (shell) of the present invention preferably comprises between about 1–20% by weight of the interior matrix.

Additives useful as filling the matrix composition of the present invention include but are not limited to: tetrakis [methylene 3,-(3'5'-di-tertbutyl-4"hydroxyphenyl) propionate]methane, octadecyl 3-(3",5"-di-tert-butyl-4"- hydroxyphenyl) propionate, distearyl-pentaerythritoldiproprionate, thiodiethylene bis-(3,5-ter-butyl-4-hydroxy)hydrocinnamate, (1,3,5-trimethyl-2,4,6-tris[3,5-di-tert-butyl-4-hydroxybenzyl]benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes (e.g. polyethylene, polypropylene, microcrystalline, carnauba, paraffin, montan, candelila, beeswax, ozokerite, ceresine, and the like), fatty acids selected from stearic acid, lauric acid, myristic acid, palmitic acid and the like, metal stearates selected from calcium stearate, magnesium stearate, zinc stearate, aluminum stearate and the like. Minor amounts of other polymers and copolymers can be melt-blended with the styrene-ethylene-butylene-styrene block copolymers mentioned above without substantially decreasing the desired properties. Such polymers include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, $(SB)_n$ styrene-butadiene and $(SEB)_n$, $(SEBS)_n$, $(SEP)_n$, $(SI)_n$ styrene-isoprene multi-arm, branched, and star shaped copolymers and the like. Still, other homopolymers can be utilized in minor amounts; these include: polystyrene, polybutylene, polyethylene, polypropylene and the like.

Examples of potentially useful and preferable shell materials are: gelatin, gum arabic, collagen, casein, polystyrene, and other art-known polymeric materials that will serve to deter migration of the fluorescent materials from the capsule. Such materials are well known in the art, including but not limited to: chitosan, polycarboxylated polymer, hydrophilic gums and hydrophilic mucilloids such as agar, alginic acid, calcium polycarbophil, carboxymethylcellulose sodium, carrageenan, chondrus, glucomannan, polymannose acetate, guar gum, karaya gum, kelp, methylcellulose, plantago seed (psyllium), polycarbophil tragacanth, pectin, tragacanth gum, xanthan gum or acidic fractions thereof, monoalkylene glycol monoester of methacrylic acid, polyalkylene glycol monoester of methacrylic acid, monoalkylene glycol monoester of crylic acid, polyalkylene glycol monoester, N-alkyl substituted acrylamide, N,N-dialkyl substituted acrylamide, N-alkyl substituted methacrylamide, N,N-dialkyl substituted methacrylamide, N-vinylpyrrolidone, alkyl substituted N-vinylpyrrolidone, vicinal epoxy alkyl 2-alkenoate, and combination thereof among them or with many other materials. For example, in addition to polystyrene, polymeric materials will include but are not limited to brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polysulfone, or combinations thereof are acceptable as well. Other materials such as carbohydrate, e.g., hydroxyethyl cellulose, proteinaceous polymers, polypeptides, lipids (liposomes), metal, resin (natural resins such as gum rosin, wood rosin, and tall oil rosin, shellac, copal, dammar, gilsonite and zein; semi-synthetic resins such as hardened rosin, ester gum and other rosin esters, maleic acid resin, fumaric acid resin, dimer rosin, polymer rosin, rosin-modified phenol resin, synthetic resins such as phenolic resin, xylenic resin, urea resin, melamine resin, ketone resin, coumarone-indene resin, petroleum resin, terpene resin, alkyl resin, polyamide resin, acrylic resin, polyvinyl chloride, vinyl chloride-vinyl acetate copolymer, polyvinyl acetate, ethylene-maleic anhydride copolymer, styrene-maleic anhydride copolymer, methyl vinyl ether-maleic anhydride copolymer, isobutylene-maleic anhydride copolymer, polyvinyl alcohol, modified polyvinyl alcohol, polyvinyl butyral (butyral resin), polyvinyl pyrrolidone, chlorinated polypropylene, styrene resin, epoxy resin and polyurethane), wax (e.g. polyethylene, polypropylene, microcrystalline, carnauba, paraffin, montan, candelila, beeswax, ozokerite, ceresine), latex, rubber (cyclized rubber, rubber chloride), silicone, e.g., polydimethyldiphenyl siloxane, glass, ceramic and the like are equally suitable. The various encapsulation techniques using these materials are well documented in encapsulation art and are familiar to those skilled in the art.

The presently preferred material for forming the matrix of capsules is polysaccharide gums, either natural or synthetic, of the type which can be gelled to form a shape retaining mass by being exposed to a change in conditions such as a pH change, temperature change, or by being exposed to cations such as $Ca^{2+}$ or $Na^+$. Thereafter, core or matrix material is permanently "cross-linked" or hardened by polymers containing reactive groups such as aldehyde, amine or imine groups which can react with essentially monomeric constituents. Thus, included within the term "encapsulation," are compositions which are coated, insofar as the coating or shell provides a physical barrier.

"Cross-linking" as used herein, refers to the linking of two or more chains of polymer molecules, by the formation of a bridge between the molecules composed of either a chemical bond, an element, a group or a compound. The terms "particle", "microparticle", "bead" as used herein, refer to an encapsulated composition, so that each capsule encapsulating such particles ranges in size from about 1 nm to about 10 mm in diameter. More preferably, such capsules range from about 1 micron to about 1,000 microns in diameter.

Fluorescent dyes used in this invention are known in the art and may have emission wavelengths between 200 nm and 1,000 nm. However, any other suitable dye can be used. For example, the squaric acid based fluorescent dyes can be synthesized by methods described in the literature. See, for example, Sprenger et al., Angew. Chem., 79, 581 (1967); Angew. Chem., 80,541 (1968); and Maaks et al., Angew Chem. Intern. Edit., 5, 888 (1966), incorporated herein by reference in their entirety. Additionally, unsymmetrically substituted squaric acid compounds can be synthesized by methods such as those described by Law et al., J. Org. Chem. 57, 3278, (1992), incorporated herein by reference in its entirety. Specific methods of making some of such dyes are well known in the art and can be found for example in U.S. Pat. Nos. 5,795,981; 5,656,750; 5,492,795; 4,677,045; 5,237,498; and 5,354,873, incorporated herein by reference in their entirety. The practical use of above described fluorescent dyes, e.g., phthalocyanines, 2,3-naphthalocyanines, squaraines and croconic acid derivatives is disclosed in U.S. Pat. No. 5,525,516 issued to Krutak et al., incorporated herein by reference in its entirety. These dyes may contain methine groups and their number influences the spectral properties of the dye. The monomethine dyes that are pyridines and typically have blue to blue-green fluorescence emission, while quinolines have green to yellow-green fluorescence emission. The trimethine dye analogs are substantially shifted toward red wavelengths, and the pentamethine dyes are shifted even further, often exhibiting infrared fluorescence emission (see for example U.S. Pat. No. 5,760,201) incorporated herein by reference in its entirety.

Related dyes can be further selected from cyclobutenedione derivatives, substituted cephalosporin compounds, fluorinated squaraine compositions, symmetrical and unsymmetrical squaraines, alkylalkoxy squaraines, or squarylium compounds. Some of these dyes can fluoresce at near infrared as well as at infrared wavelengths that would effectively expand the range of emission spectra up to about 1,000 nm. In addition to squaraines, i.e., derived from squaric acid, hydrophobic dyes such as phthalocyanines and naphthalocyanines can be also selected as operating at longer wavelengths. Other classes of fluorochromes are equally suitable for use as dyes according to the present invention. Non-limiting examples of some of these dyes are listed herein: 3-Hydroxypyrene 5,8,10-Tri Sulfonic acid, 5-Hydroxy Tryptamine, 5-Hydroxy Tryptamine(5-HT), Acid Fuchsin, Acridine Orange, Acridine Red, Acridine Yellow, Acriflavin, AFA (Acriflavin Feulgen SITSA), Alizarin Complexon, Alizarin Red, Allophycocyanin, ACMA, 4-dicyano-methylene-2-methyl-6-(p-dimethylaminostyryl)4H-pyran, fluorescent chelates of lanthanide ions, for example ions of Terbium, Samarium, and Europium, Aminoactinomycin D, Aminocoumarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy F1, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow Ci, Lucifer Yellow VS, Magdala Red, Marina Blue, Maxilon Brilliant Flavin 10 GFF, Maxilon Brilliant Flavin 8 GFF, MPS(Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof.

One skilled in the art would certainly know which one to select among such dyes as long as desired emission and absorption properties as well as their hydrophobic or hydrophilic properties are appropriate.

One skilled in the art would certainly know to select instead of above listed dyes so-called man-made "quantum dots" or "semiconductor nanocrystals", which usually consist of sulfide (S) or selenium (Se) of various metals such as Zn, Cd, Pb, Sn, Hg, Al, Ga, In, Ti, Si, Ag, Fe, Ni or Ca. The means of making quantum dots are well known in the art as disclosed, for example, in U.S. Pat. Nos. 5,906,670; 5,888, 885; 5,229,320; and 5,482,890, which are incorporated herein by way of reference. Other metals are known which can fluoresce when in a chelated form (e.g., EDTA) and may include but are not limited to metals such as Tc, In, Ga, Sc, Fe, Co, Pr, Nd, Sm, Eu, Gd, Th, Dy, Ho, Er, Tm and Yb (e.g., U.S. Pat. Nos. 4,454,106 and 4,374,120) incorporated herein by reference in their entirety.

Furthermore, naturally occurring minerals and crystals such as Clinohedrite, Hardystonite, Willemite, Witherite, Yellow Calcite, Tan Calcite, Terlingua Calcite, Amber, Scapolite, and Eucryptite among others, are also known to fluoresce when exposed to a short-wave high-energy excitation light (detailed list of some of such minerals can be found in U.S. Pat. Nos. 4,365,153; 4,336,459; and 4,236, 071, which references are incorporated herein by way of reference). Specifically, minerals that are known to fluoresce in a blue spectrum include but are not limited to Benitoite, Hydrozincite, and Scheelite; those that emit green fluorescence include Chalcedony Rose, Hyalite Opal, Youngite, those that emit red fluorescence include Eucryptite, those that emit orange fluorescence include Halite, Svabite-Tilisite. There are also some minerals, which may, for example, emit fluorescent light in two separate light spectra such as Phlogopite/Diopside (yellow/blue colors respectively). Such minerals are used as such in crystalline form or can be ground into fine powders.

Preferably, fluorescent materials of the invention are present in the form of spherical microparticles or crystals or nanocrystals such as quantum dots. Physical shapes other than spherical particles, crystals, and powders can be incorporated within a shell barrier. One skilled in the art may utilize fluorescent fibers such as disclosed, for example, in U.S. Pat. No. 4,921,280, as incorporated herein by way of reference. Encapsulated fluorescent materials of the invention may also include light-excitable materials such as used in liquid crystal display (LCD) devices, which are disclosed in U.S. Pat. Nos. 3,998,526; 4,337,999; 4,425,029; 4,668, 049; 5,039,206; and 5,052,784, as incorporated herein by way of reference.

The spectral properties of the fluorescent materials should be sufficiently similar in excitation wavelengths and intensity to fluorescein or rhodamine derivatives as to permit the use of the same flow cytometry equipment. More preferably, the dyes have the same or overlapping excitation spectra, but possess distinguishable emission spectra. Any detection system can be used to detect the difference in spectral characteristics between the two dyes, including a solid state detector, photomultiplier tube, photographic film, or eye, any of which may be used in conjunction with additional instrumentation such as a spectrometer, luminometer microscope, plate reader, fluorescent scanner, flow cytometer, or any combination thereof, to complete the detection system. Preferably, dyes are chosen such that they possess substantially different emission spectra, preferably having emission maxima separated by greater than 10 nm, more preferably having emission maxima separated by greater than 25 nm, even more preferably separated by greater than 50 nm. When differentiation between the two dyes is accomplished by visual inspection, the two dyes preferably have emission wavelengths of perceptibly different colors to enhance visual discrimination. When it is desirable to differentiate between the two dyes using instrumental methods, a variety of filters and diffraction gratings allow the respective emission maxima to be independently detected. When two dyes are selected that possess similar emission maxima, instrumental discrimination can be enhanced by insuring that both dyes' emission spectra have similar integrated amplitudes, similar bandwidths, and the instrumental system's optical throughput be equivalent across the emission range of the two dyes. Instrumental discrimination can also be enhanced by selecting dyes with narrow bandwidths rather than broad bandwidths, however such dyes must necessarily possess a high amplitude emission or be present in sufficient concentration that the loss of integrated signal strength is not detrimental to signal detection.

The invention described herein is further exemplified in the following Examples. While these Examples provide a variety of combinations useful in performing the methods of the invention, they are illustrative only in regard to some of the materials useful in (his invention and are not to be viewed as limiting in any manner the scope of the invention.

6. EXAMPLES

6.1 Example 1

Gum Arabic Encapsulation

One gram of red fluorescent nanospheres (40 nm diameter) is mixed with one gram of orange fluorescent nanospheres (40 mm diameter) in 9 ml of hexane solvent. Instead of nanospheres stained with fluorescent dyes, powdered fluorescent minerals of desired color can be selected. For example, Hardystonite emits blue fluorescent light, while Clinohedrite is orange; Calcite is red; and Willemite provides fluorescent light in green spectra. Alternatively, a mixture of two types of CdSe—CdS nanocrystals can be used. One gram of CdSe—CdS nanocrystals of about 2 nm size (emitting green fluorescent light) and one gram of red fluorescent CdSe—CdS nanocrystals (about 4 run diameter) are mixed in n-butanol. Another mixture of fluorescent materials comprises green fluorescent material such as ZnS:Cu, Al, the blue fluorescent material ZnS:Ag, Cl, and the red fluorescent material such as $Y_2O_2S$:Eu, CdS alloy.

These materials may be dissolved in other organic solvents that are equally suitable including but not limited to: benzene, toluene, xylene, cyclohexane, hexane, ligroin, methyl isobutyl ketone, methyl acetate, ethyl acetate, butyl acetate, methyl CELLOSOLVE, ethyl CELLOSOLVE, butyl CELLOSOLVE, diethylene glycol monobutyl ether, diethylene glycol monobutyl ether acetate, methanol, ethanol, n-propyl alcohol, isopropyl alcohol, n-hexanol, cyclohexanol, 2-ethylhexyl alcohol, or combination thereof.

The mixture of such materials is then emulsified with 30 g of commercially available 10% aqueous gelatin solution. The rate of mixing controls final particle size; faster mixing yields smaller capsules. To this is added 30 g of a 10% aqueous gum arabic solution. The solution is warmed to 40° C. and 140 ml of water at the same temperature is added. Next 3 to 6 ml of 10% aqueous acetic acid are added to adjust the pH to between 4.0 and 4.4. The system is then cooled to 5° C. and 1 ml of 30% cross-linking agent, formalin, is added, followed by 10% NaOH to obtain a pH of 9. The temperature is then slowly raised to 50° C. to complete the curing of the capsule shell.

6.2 Example 2

Collagen Encapsulation

Vitrogen solution comprising 0.3% collagen solution at pH 2.0 is dialyzed against dilute acetic acid at pH 4.5, until the solution reached a pH of 4.4–4.6, followed by adjustment of the pH to 3.5 using IM acetic acid and then back to pH 4.5 using 1N sodium hydroxide, followed by pH adjustment to approximately 10 with 1N NaOH, followed by adjustment to pH 6.7 using 1N acetic acid. The resulting collagen solution thus contains a high concentration of sodium acetate. Collagen nucleation/precipitation is measured spectrophotometrically as an increase in absorbance at 530 nm. Collagen in dilute organic acid solution shows a higher levels of light defraction, indicating a greater level of collagen fibril formation, and larger fibrils.

A sample of fluorescent microparticles, beads, or crystals such as disclosed in Example 1 are brought into an alginate matrix, washed twice by suspending them in 2 mM $CaCl_2$ solution. These particles are then twice washed by suspending in 18.5% sucrose/2 mM $CaCl_2$ solution. The beads are suspended in an equal volume of sucrose solution with 0.5 M 2-(N-morpholino)-ethane sulfonic acid buffer at pH 6.0. A 0.3% collagen solution in dilute acetic acid, pH 4.5 is added to the bead suspension to achieve approximately 1 g/ml of collagen. 1 M NaOH is added to bring the suspension pH to from about 6.5 to about 7.0. The bead suspension is then rotated for 1 hour at room temperature on a test tube rotator. Next, the bead suspension is diluted with 9.25% sucrose solution. The diluted suspension is centrifuged, washed and 1-ethyl-3-(−3dimethylaminopropyl) carbodiimide hydrochloride (EDC) cross-linking solution is added to yield a final EDC concentration of 2–4 mg/ml. The beads are vortexed immediately, and shaken for 10–20 minutes. The beads are then diluted in media, supplemented with 4 mM $CaCl_2$, 0.5% gelatin, washed, and resuspended in the same media. Comparison of encapsulated beads to uncoated beads shows that collagen-coated beads are resistant to the leakage of fluorescence as compared to uncoated fluorescent beads.

In addition to commercially available collagen types, it may also be appreciated that derivatized collagen is equally suitable to the present invention. Polymer derivatization is well known in the art, and may allow for the alteration of the properties of the particular polymer used, e.g., improved nucleation, better stability of crosslinked forms, alteration of nucleation pH profiles, etc. Examples of derivatized collagen include pegylated collagen (collagen to which polyethylene glycol has been covalently attached), succinylated collagen, alkylated collagen (e.g., methylated), aminated collagen, activated aldehyde derivatized collagen, and the like. See, e.g., U.S. Pat. No. 4,164,559, incorporated by reference herein.

6.3 Example 3

Chitosan Encapsulation

Chitosan is obtained by acid hydrolysis of chitin (poly-D-N-acetylglucosamine), the primary building material of invertebrate exoskeletons. Chitosan is a long chain, aminated polymer which is only slightly soluble in water but can be readily dissolved in dilute acetic acid. Stock solutions of chitosan (CSN, Sigma Chemical Co.) is mixed with fluorescent particles to be encapsulated, forming a solution or slurry. Droplets of the chitosan and fluorescent core material suspension are formed by any conventional droplet-forming apparatus, such as, for example, described in U.S. Pat. No. 4,803,168 to Jarvis, Jr., incorporated by reference in its entirety. The preferred multivalent gelling solution is a 125 mM $NaHPO_4$ solution, but monobasic or dibasic sodium phosphate and sodium sulfate solutions are also acceptable temporary matrices. Temporary matrices formed by this process are collected and washed to remove excess gelling solution. The matrices are then subjected to a coating or cross-linking solution of a polyanionic, preferably chitosan, acrylic acid ester and methacrylic acid ester polycarboxylated polymer. A preferred cross-linking solution is a 1% solution of poly-L-aspartic acid or poly-L-glutamic acid, diluted 1:15 with 150 mM sodium chloride and reacted for 3–6 minutes at ambient room temperature. Obtained capsules are substantially spherical, about 300–500 microns in diameter. Capsules formed by this process are stable in aqueous environment, are not "sticky" and have no tendency towards clumping. Porosity of the capsules is controlled by cross-linking reaction time.

6.4 Example 4

Cellulose Encapsulation

Approximately 1073 grams of tertiary amine oxide such as N-methylmorpholine-N-oxide in water (76% NMMO, 24% $H_2O$), 16 g of cellulose (DP=625, 5% moisture content) and 1.5 g stabilizer, e.g., gallic acid propyl ester, are prepared in a container and heated to above 72° C. This solution is stirred for approximately 15 minutes and about 100 g of water is then separated under vacuum. After water removal step a clear cellulose solution is obtained. Alternatively, 554 g of NMMO/water mixture (83% NMMO), 0.8 g stabilizer and 11.3 g cellulose are prepared in a container and heated to approx. 95° C. while being stirred simultaneously. After approximately 30 to 60 minutes a cellulosic solution is obtained. In this procedure it is no longer necessary to separate the water.

Fluorescent microparticles are added to cellulose solution containing a sufficient amount of cellulose so that encapsulated solid particles during dispersion exhibit at least a monomolecular layer of cellulose over the entire surface. Encapsulated microparticles are then formed from the liquid dispersion by spraying method as disclosed for example in U.S. Pat. No. 5,895,795, incorporated herein by way of reference. The viscosity of cellulose plays a role so that it is possible to control the shape of the discrete microcapsules by adjusting the viscosity, e.g., by varying the concentration of the cellulose employed. Also by means of other additives the form of the particles obtained during the spray process can be influenced. Thus, it is possible to produce discrete shell-coated particles with a spherical, granular, rod-like shape, etc.

6.5 Example 5

Liposome Encapsulation

Lipid films containing egg sphingomyelin, cholesterol, stearic acid and dipalmitoylphosphatidylethanolamine mixture are prepared on the walls of 10 ml pear-shaped flasks and dried overnight. The procedure of making liposomes is well established in the art and can be found for example in U.S. Pat. No. 5,017,501, which incorporated herein by way of reference. To each flask is added 2.4 g of 50–100 micron diameter glass beads and 2 ml buffered solution containing a precisely defined mixture of two populations of microparticles dyed with two distinct fluorescent dyes. The flasks are stoppered and vortexed 2100 rpm for 5, 10, and 45 minutes, respectively. The liposomes are then aspirated away from the settled glass beads. Buffer is added to wash the beads twice to recover all the liposomes. Any non-encapsulated free fluorophore-stained microspheres are removed from the liposome-encapsulated preparations by washing with a solution containing 88 mM NaCl, 50 mM maltose, 0.02% thimerosal and 50 mM HEPES at pH 7.0. The liposome preparation is pelleted at 48,000 g for 45 minutes and the supernatant removed. The liposomes are then resuspended and the washing procedure repeated about 3 times. The mean diameter of liposome capsules is controlled by vortexing time since mean diameter decreases at longer vortexing times. Signal-to-noise, trapped volume and encapsulation rate increases as a function of vortexing time. The trapped volume decreases and encapsulation rate increases at higher lipid concentrations.

6.6 Example 6

Resin Encapsulation

Microcapsules containing multicolored fluorescent particles and having a wall film of melamine-formaldehyde resin are prepared as follows: To 200 ml of 3.0% aqueous solution of ethylene-maleic anhydride copolymer (EMA-31, Monsanto Co., Ltd.) a 20% aqueous solution of sodium hydroxide is added to adjust the pH to 6.0. To this solution a desired amount of fluorescent beads is added and solution is stirred at about 60° C. Separately, to 45 ml of 37% aqueous solution of formaldehyde 15 ml of melamine is added and the mixture is reacted at 60° C. for 15 minutes to prepare a prepolymer solution. The prepolymer solution is then added dropwise to the solution of fluorescent microparticles and 0.1N HCl is added dropwise thereto while stirring to adjust the pH to 5.3, and the mixture is heated to 80° C. and maintained at that temperature for about one hour. Then 0.2N HCl is added to adjust the pH to 3.5, and the mixture is reacted for another 3 hours, and allowed to cool to obtain a capsule dispersion containing particles of about 2.3 microns in average size. The dispersion is filtered, washed with ethanol, and is ready for use.

While the invention has been described in connection with specific embodiments thereof, it will be understood that it is capable of further modifications and this application is intended to cover any variations, modifications, uses, or adaptations of the invention following, in general, the principles of the invention and including such departures from the present disclosure as come within known or customary practice within the art to which the invention pertains and as may be applied to the essential features herein before set forth and as follows in the scope of the appended claims. All publications and patent documents cited in this application are incorporated by reference in their entirely for all purposes to the same extent as if each individual publication or patent document were so individually denoted.

What is claimed is:

1. A composition comprising at least two types of discrete fluorescent materials, each capable of emitting a distinct fluorescent light signal, said discrete fluorescent materials encapsulated by a shell barrier.

2. The composition of claim 1 wherein the discrete fluorescent materials comprise microspheres or nanospheres.

3. The composition of claim 1 wherein the discrete fluorescent materials comprise powders, crystals, rods, fibers, liquid, or a combination thereof.

4. The composition of claim 1 wherein the shell barrier comprises a layer of a polymerizable material.

5. The composition of claim 1 wherein the composition exhibits a spherical shape or a granular shape.

6. The composition of claim 1 whereby said composition has a diameter of about 1 nanometer to about 10 millimeters.

7. A fluorescence encapsulation device comprising an inner zone delimited by a capsule shell that inhibits the leakage of fluorescence emitting materials, wherein the capsule shell comprises a hydrophilic or hydrophobic polymer material, wherein the inner zone comprise two or more fluorescent light emitting materials each capable of emitting at least one distinct fluorecent signal.

8. A method of making a matrix, which emits at least two distinct light signals, the method comprising the steps of:
   a) mixing in a matrix-forming material at least two light emitting materials at a desired ratio; and
   b) polymerizing the mixture obtained at step (a) to form the matrix, where said polymerizing will deter leakage of the at least two light emitting materials out of the matrix.

9. A process for encapsulating two or more fluorescent materials, each capable of emitting at least one distinct fluorescent signal, in a shell comprising:
   a) dispersing or dissolving said two or more fluorescent materials in a matrix-forming material;
   b) adding a shell material or precursor thereof to the two or more fluorescent materials in the matrix-forming materials; and
   c) polymerizing the shell material or its precursor to a polymerized shell which encapsulates the two or more fluorescent materials.

10. A process for encapsulating fluorescent materials in capsule shell, wherein the capsule shell emits two or more distinctive fluorescent signals, the process comprising:
    a) preparing an encapsulation composition by dispering or dissolving said fluorescent material in a matrix-forming material,
    b) emulsifying the encapsulation composition in a solution of gelatin,
    c) mixing at desired rate the obtained solution to allow said encapsulation composition to break up into droplets of desired size,
    d) adding a solution of gum arabic,
    e) thermally softening the obtained solution while adding warm water,
    f) bringing the pH of the solution to about 4.0 and 4,4,
    g) cooling the solution and adding a cross-linking agent to form the capsule shell,
    h) bringing the pH to about 9, and;
    i) curing the capsule shell by raising the temperature to about 50° C.

11. A composition comprising (i) two or more substances, each substance capable of emitting a distinctive fluorescent signal, and (ii) a shell barrier encapsulating said two or more substances.

12. The composition of claim 11 in which said fluorescent signal is distinctive by way of its wavelenght.

13. The composition of claim 11 in which said flourescent signal is distinctive by way of its intensity.

14. The composition of claim 11 in which said flourescent signal is distinctive by way of its wavelenght, intensity, or both.

15. The composition of claim 11 in which said each substance comprises one or more particles each stained with a fluorescent dye.

16. The method of claim 8, wherein an outer surface of the matrix consitutes a barrier encapsulating the at least two light emitting materials.

17. The method of claim 8, wherein said mixing comprises dispersing the at least two light emitting materials in the matrix-forming material.

18. The method of claim 8, wherein the at least two light emitting materials comprises soluble or insoluble fluorescent materials.

19. The method of claim 8, wherein the at least two light emitting materials are presented as spheres, powders, crystals, rods, fibers, liquids, or a combination thereof.

20. The method of claim 8, wherein said polymerizing comprising crosslinking the mixture to form solid particles of the matrix.

21. The method of claim 8, further comprising mixing in the matrix-forming material additional components that will further deter the leakage of the at least two light emitting materials out of the matrix.

22. The method of claim 8, wherein the at least two distinct light signals have precisely controlled intensities.

23. A matrix, comprising:
    a polymerized matrix-forming material; and
    at least two light emitting materials contained within the polymerized matrix-forming material, wherein polymerization of the matrix-forming matrial deters leakage of the at least two light emitting materials out of the matrix.

24. The matrix of claim 23, wherein an outer surface of the matrix constitutes a barrier encapsulating the at least two light emitting materials.

25. The matrix of claim 23, wherein the at least two light emitting materials comprise soluble or insoluble fluorescent materials.

26. The matrix of claim 23, wherein the at least two light emitting materials are presented as spheres, powders, crystals, rods, fibers, liquids, or a combination thereof.

27. The matrix of claim 23, wherein the polymerized matrix-forming material comprises a crosslinked matrix-forming material that forms solid particles of the matrix.

28. The matrix of claim 23, further comprising additional components contained within the polymerized material-forming material that will further deter the leakage of the at least two light emitting materials out of the matrix.

29. The matrix of claim 23, wherein the at least two light emitting materials emit distinct light signals having precisely controlled intensities.

* * * * *

UNITED STATES PATENT AND TRADEMARK OFFICE
CERTIFICATE OF CORRECTION

PATENT NO. : 6,905,766 B2
DATED : June 14, 2005
INVENTOR(S) : Chandler

It is certified that error appears in the above-identified patent and that said Letters Patent is hereby corrected as shown below:

Title page,
Item [74], *Attorney, Agent, or Firm*, delete "Charles D. Hustop" and substitute
-- Charles D. Huston --.

Column 13,
Line 17, delete "comprise" and substitute -- comprises --.

Signed and Sealed this

Twenty-eighth Day of March, 2006

JON W. DUDAS
*Director of the United States Patent and Trademark Office*